Dec. 13, 1960 O. O. DUNHAM Plant Pat. 2,003
CHRYSANTHEMUM PLANT
Filed July 27, 1959
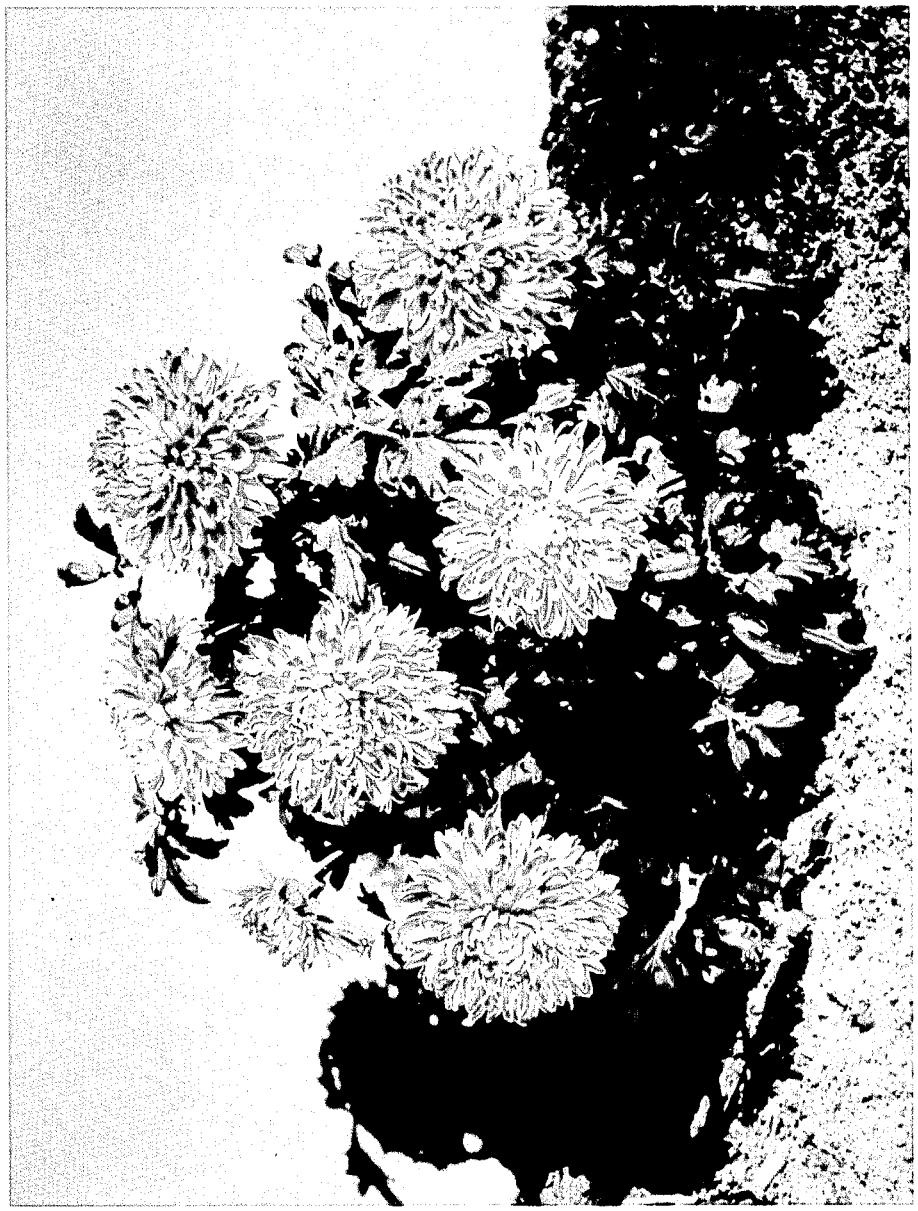
Inventor
O. O. Dunham
by Robb & Robb
attorneys United States Patent Office Plant Pat. 2,003
Patented Dec. 13, 1960

2,003

CHRYSANTHEMUM PLANT

Orville O. Dunham, Niles, Mich., assignor to George J. Ball, Inc., West Chicago, Ill., a corporation of Illinois Filed July 27, 1959, Ser. No. 829,945

1 Claim. (Cl. 47—60)

My present invention comprises a new and distinct variety of chrysanthemum plant, which is the result of crossing the variety known as "Fred Yule" an unpatented variety, with the unpatented variety which I have identified as "No. 5350."

The object of this invention has been to produce a new variety of chrysanthemum of the indicum type having blossoms of a generally brown-reddish orange to dark reddish orange in aspect and of large size (Nickerson Color Fan produced by Munsell Color company).

The development of my present new variety, has been the result of a careful program conducted of selection and cross-breeding with the view of producing new varieties of chrysanthemums of the indicum type which are of more continuous flowering habit and earliness of flowering than the parents with an improvement in the color over either of the parents particularly the parent "Fred Yule."

A result of the specific hybridization previously mentioned has been to produce my present new and distinct variety of chrysanthemum plant, which is characterized as to novelty by the strong reddish-orange color of its blooms, the very double arrangement of its petals, the vigorous, more compact habit of growth, the very large size of its blooms and the early, continuous and long blooming period.

It may be more specifically stated that the blooms of my new variety have a more orange color than the parent "Fred Yule" from which the instant variety obtained this desirable characteristic.

While this new variety bears a closer resemblance to the parent "Fred Yule" than to the other parent "No. 5350," the new variety differs from both parents and some other known varieties in many respects.

Comparing the color of the bloom of my new variety with the color of the blooms of the variety "Fred Yule" it may be noted that the color of the blooms of the latter are more reddish than are the blooms of the variety under consideration. Whereas the variety "Fred Yule" is a somewhat taller plant than the instant variety, the characteristics of both parents are taken advantage of to produce a more continuous flowering habit and earliness of flowering from the parent "No. 5350."

Under conditions of culture which have taken place in the region of Niles, Michigan, plants of my new variety have produced blooms averaging some seven inches in diameter and whereas the parent "Fred Yule" is somewhat taller, this variety is shorter as before mentioned.

The pollen parent "Fred Yule" contributes the color primarily, whereas the seed parent "No. 5350" has supplied the continuous flowering and earliness of bloom.

When the variety is grown in the region of Niles, Michigan, the blooms begin to appear early in September and are continuous in nature until a killing frost with a profuse production of blooms being characteristic.

The plants are of much more compact habit than the English chrysanthemum and no staking is required.

My new variety has been asexually reproduced by cuttings in the vicinity of Niles, Michigan.

My new variety has been found to retain its distinctive characteristics through successive asexual reproduction.

The accompanying drawing, forming a part hereof, shows a typical plant of my new variety of chrysanthemum.

The following is a detailed description of my new variety of chrysanthemum plant, the color references being to the Nickerson Color Fan produced by Munsell Color Company:

Classification: Botanic—*Chrysanthemum indicum.*

*Flower*

Blooming habit: Blooms profusely and continuously from early in September until a killing frost. Observations were made at Niles, Michigan, in September.

Bud:
- *Size.*—Large.
- *Form.*—Short with flat top. Not affected by wet weather. Not affected by hot weather.
- *Peduncle.*—Very long.
- *Aspect.*—Rough.
- *Color.*—Medium green.
- *Strength.*—Stiff; erect.
- *Opening.*—Bud opens well; somewhat affected by adverse conditions.

Bloom:
- *Size.*—Very large.
- *Average size when fully expanded.*—7 inches (disbudded).
- *Borne.*—In clusters; irregular.
- *Stems.*—Long; strong.
- *Form.*—When first open—flat. Permanence—retains its form to the end.
- *Petalage.*—Very double. Number of petals under normal conditions—innumerable.
- *Color.*—Bud: When petals begin to unfurl—5R 4/12—red. When half blown—inside of petals—2.5YR 6/12 washed with 10R 5/11; reverse of petals—2.5Y 8/12 washed with 2.5YR 5/9.
- *Color.*—Bloom: Center of flower—between 5YR 7/11 and 5YR 6/11. Outer petals—between 7.5R 6/12 and 7.5R 5/13. Base of petals (singlet)—between 7.5R 6/12 and 7.5R 5/13. Inside of petals—between 7.5R 6/12 and 7.5R 5/13. Reverse of petals—between 7.5R 6/12 and 7.5R 5/13. General tonality from a distance—between 10R 6/12 and 10R 5/11.
- *Discoloration.*—First week—retains same color. Second week—somewhat the same color. Third week—retains somewhat the same color. Light frost tends to intensify colors.

Petals:
- *Texture.*—Thin. Affected by bleaching in hot weather. Affected by some fungus infection in wet weather.
- *Appearance.*—Velvety inside—satiny outside.
- *Form.*—Pointed.
- *Arrangement.*—Imbricated.
- *Persistence.*—Hang on and dry.
- *Lastingness.*—On the plant—very long. As cut flower—long.

Genital organs:
- *Stamens, anthers.*—Small; few. Color—yellow. Arrangement—regular around styles.
- *Stamens, filaments.*—Short. Color—white.
- *Styles.*—Columnar. Length—short.
- *Stigmas.*—White.
- *Ovaries.*—All enclosed in calyx.

Fruit: Variety is fertile with its own pollen.

*Form.*—Oblong shaped.

*Aspect.*—Rough.

*Color at maturity.*—Brownish grey.

*Plant*

Form: Bush.

Growth: Vigorous, dwarf, branching, compact.

Foliage:

*Size.*—Large.

*Quantity.*—Abundant.

*Color.*—New foliage: upper side—normal green; under side—light green. Old foliage: upper side—dark green; under side—dark green.

*Shape.*—Three lobed.

*Texture.*—Upper side—velvety; flat. Under side—velvety. Ribs and veins—ordinary.

*Edge.*—Smooth.

*Leaf stem.*—Green in color. Under side—smooth.

*Stipules.*—Short.

*Disease resistance.*—Under certain conditions susceptible to mildew.

I claim:

A new and distinct variety of chrysanthemum plant substantially as herein disclosed, characterized as to novelty by the strong reddish orange color of its blooms, the very double arrangement of its petals, the vigorous, more compact habit of growth, the very large size of blooms, and the early, continuous and long blooming period.

No references cited.